| United States Patent [19] | [11] Patent Number: 4,675,381 |
| Bichon | [45] Date of Patent: Jun. 23, 1987 |

[54] BIODEGRADABLE POLYPEPTIDE AND ITS USE FOR THE GRADUAL RELEASE OF DRUGS

[75] Inventor: Daniel Bichon, Gaillard, France

[73] Assignee: Battelle Memorial Institute, Geneva, Switzerland

[21] Appl. No.: 711,469

[22] PCT Filed: Apr. 2, 1984

[86] PCT No.: PCT/CH84/00052

§ 371 Date: Feb. 28, 1985

§ 102(e) Date: Feb. 28, 1985

[87] PCT Pub. No.: WO85/00372

PCT Pub. Date: Jan. 31, 1985

[30] Foreign Application Priority Data

Jul. 1, 1983 [CH] Switzerland ............... 3619/83

[51] Int. Cl.[4] ............... B07K 7/00; C08H 1/00; C08G 69/10
[52] U.S. Cl. ............... 530/345; 528/328; 528/329.1; 526/238.1; 604/890; 424/484
[58] Field of Search ............... 260/112.5 R; 528/328, 528/329; 424/19–21; 604/890; 526/238.1; 530/345

[56] References Cited

U.S. PATENT DOCUMENTS

| 3,230,274 | 1/1966 | Garber et al. | 528/328 |
| 3,371,069 | 2/1968 | Miyamae et al. | 528/328 |
| 4,351,337 | 9/1982 | Sidman | 424/22 |

OTHER PUBLICATIONS

Williams, "Review Biodegradation of Surgical Polymers", *J. of Material Science* 17 (1982) pp. 1233–1246.
Yoshida et al., "In Vivo Controlled Release ... Tablets" CA#223180s, vol. 96 1982.
Dickinson et al., Biodegradation of a Poly-(αAmino Acid) Hydrogel", *J. Biomed. Mater. Res.* vol. 15, 1981, pp. 591–603.
Wood, Biodegradable Drug Delivery Systems" *Inter. J. Pharmaceutics* 7, 1980, pp. 1–18.

*Primary Examiner*—Maurice J. Welsh
*Assistant Examiner*—Garnette D. Draper
*Attorney, Agent, or Firm*—Cushman, Darby & Cushman

[57] ABSTRACT

Biodegradable acyloxymethyl polyaspartate and polyglutamate as drug carrier in an encapsulated or incorporated state in the matrix of the copolymer. The polypeptide loaded in this way decomposes enzymatically in the organ where it has been placed and thus progressively releases the drug which it contains.

11 Claims, No Drawings

BIODEGRADABLE POLYPEPTIDE AND ITS USE FOR THE GRADUAL RELEASE OF DRUGS

The subject of the present invention is a new biodegradable esterified polypeptide in which drugs can be incorporated, the drugs then being gradually released in proportion to the biochemical degradation of the polymer.

Non-toxic biodegradable polymers have been known for several years which can act as a reservoir of drugs and which allow for the controlled gradual release of the latter into the organism at the time of the degradation of the carrier polymer. General information on products of this type can be found in the work: "Fundamental Aspects of Biocompatibility" by D. F. WILLIAMS. CRC Press (1981). See also U.S. Pat. No. 4,093,709.

Of these polymers, those which are referred to in particular are synthetic polypeptides (polyamino acids), the structure of which is related to that of proteins. These polypeptides are biocompatible and the products of their degradation (amino acids) can be reabsorbed by the organism. Thus SIDMAN et al (J. Membr. Sci (1980), 7(3), 277-91) disclosed a copolymer of glutamic acid and of ethyl γ-glutamate, of which the rate of degradation is a function of the composition of the copolymer (molar proportions of the esterified segments as a ratio of the non-esterified segments) and which can store numerous medicinal products, more particularly steroids, peptides, and anti-malaria, anti-cancer and other products. Polymers of this type can be used in the form of sticks containing, mixed therewith, the desired drug, or in the form of capsules enclosing the drug if the latter cannot be mixed with the polymer.

In spite of the interest attached to the above product, there is still a search for a product with improved qualities which has the following properties in particular:

1. Excellent solubility in most conventional harmless solvents suitable for drugs (in fact known derivatives of polyaminoacids are not generally soluble in certain specific solvents (DMF, pyridine, $F_3CCOOH$), the use of which is not suitable for pharmaceutical products).
2. Thermoformability. The synthetic polypetides which are known at present cannot in fact be generally mixed with conventional biocompatible plasticizers (polyalkylene glycols) and are consequently not thermoplastic.
3. Improved control of the process of degradation. In fact, the rate of degradation of known synthetic polypeptides is linked in a manner which is difficult to reproduce to their chemical structure, more particularly to the rate of esterification. Thus in a given case (see SIDMAN K. R. et al., Publication PB 81-132136 NTIS (1980) p. 42) a variation in the rate of esterification of the order of 10% causes the rate of degradation to increase from 1 to a hundredfold (see also the reference: SIDMAN mentioned above).

The polymer of the invention allows these improvements to be put into effect. It is an esterified polypeptide with the formula:

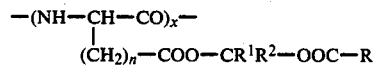

(I)

in which $R^1$ and $R^2$ are alkyl groups or hydrogen and R a substituted or non-substituted aliphatic or aromatic residue, or $R^2$ is hydrogen and an alkyl and $R^1$ and R linked to one another are substituted or non-substitued methylene or methenyl groups, n being equal to 1 or 2 and x being such that the molecular weight is at least 5000 D.

As can be seen from formula 1, the polymer of the invention is a polyaspartate or polyglutamate esterified by a derivative of acyloxymethanol ($HO—CR^{1}-R^2—OOCR$) in which R is either any organic residue, or is linked to $R^1$ so as to form a cycle. The use of the word "any" means that the nature and the structure of the R group is not critical and, for instance, there has been no case in which if R is part of the conventional compound with an RCOO-group the corresponding constituent of the invention could not be obtained. However, it is preferred to use compounds in which R is a substituted or non-substituted aliphatic or aromatic group, the substitutes being chosen from amongst the biocompatible organic groups. From amongst the preferred R groups, are the groups methyl, ethyl, propyl, isopropyl, isobutyl, tert-butyl, phenyl, benzyl and other similar groups. Of course, other groups are possible, but it is clear that the inventor has not been able to consider them all during the limited period of time available to him.

When R and $R^1$ are linked together so as to form a carbon-carbon link which may or may not be saturated, these carbon atoms may or may not be substituted by aliphatic or aromatic residues. Below are some non-limitative examples of these ester-lactal groups

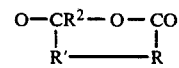

which are substituted or not corresponding to the above-mentioned definition: dimethylene group —CH$_2$—CH$_2$—; dimethylethylene group —CH(CH$_3$)—CH(CH$_3$)—; vinylene group —CH=CH—;

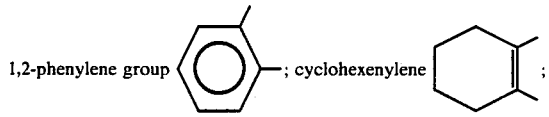

cyclopentadienylene and others.

The polymer of the invention may also be in the form of a copolymer with other polyaminoacids. In this case, there would be a copolymer with the formula:

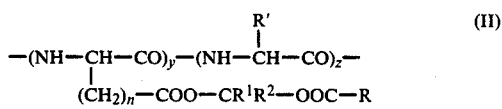

(II)

in which R is a residue of any amino acid which may or may not be esterified, the R' groups of the units —(N-

H—CHR'—CO)— may be identical or different in the copolymer chain, with $y+z=x$, y and z being integers and the value of x being always chosen so that the copolymer has an average molecular mass of at least 5000 D. Of course, if R' is identical to the group —(CH$_2$)—COO—CR$^1$R$^2$—OOC—R, the n's being different however (one of them being equal to 1 and the other being equal to two), an esterified copolymer of a glutamic and aspartic acid would be obtained. However, in general it is preferred to have different groupings for R', such as, for example, methyl (alanine), isopropyl (valine). isobutyl (leucine and isoleucine), benzyl (phenylalaline), etc. All other amino acids are, in principle, possible although for obvious reasons, it has not been possible to try all of them. R' can also designate a residue of glutamic or aspartic acid which is not esterified or partially esterified by any alcohol for example MeOH or EtOH, that is, for example, —(CH$_2$)—$_n$—COOH or —(CH$_2$)$_n$—COOMe.

It is equally possible to have amino acids of the L or D series. The amino acids of the L series (or natural acids) are the most interesting since the polypeptides which contain them are degradable by enzymes (proteases) of the human body, whilst the polypeptides consisting of D units are not. This difference can be exploited using copolymers comprising D and L amino acids with the aim of obtaining polymers of which the rate of degradation has been altered.

Returning to more general considerations, it should be noted that the molar ratio, in the copolymer II, of the other free or partially esterified polyamino acid, also allows for the regulation to a considerable degree of the rate of biodegradation of the copolymer as a function of the agents present in the organism at the target site of the mixture of copolymer and of the drug to be administered, (i.e. in the organ where the drug is to act). Thus, for example, if the copolymer is a copolymer of polyglutamate I and of leucine, the relative molar preparation of the two consituents as a function of the relative rate of degradation would be selected, at the place in question, from polyglutamate and polyleucine. In general, the ratio z/y can vary by 1 to 30, but these limits may be exceeded if necessary. Of course, in cases where the R' group does not designate a single natural group in the copolymer chain. that is for example when one R' designates a residue of free amino acid and another R' designates a residue of esterified amino acid. For greater convenience the variants of R' could be designated by the signs R', R'", etc. The general formula of a copolymer of this type can be illustratd as follows:

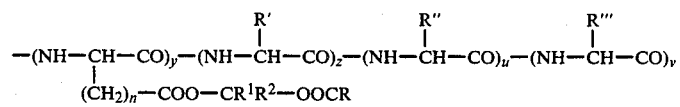

where the sum of y, z, u, v, ..., etc. is equal to x; u, v, etc. may of course be nil if the residue designated by R' is of the natural type. A typical case where the copolymer has R' and R" distinct is that in which these groups designate residues of glutamic and/or aspartic acid which may be esterified or non-esterified, the diagrammatic formula of a polymer of this type (in special cases partially methylated) is as follows:

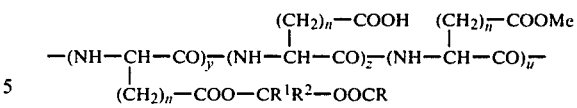

The nature of the R group can also influence the rate of degradation of the polymer I. Thus, for example, if R is a large or crowded group (for example tert-butyl), the degradation will be slower than with a methyl or ethyl group.

It is understood that, from the point of view of optical isomerism, the polymers of the invention may comprise elements of L or D configuration or racemic mixtures or even polymers where one of the configurations is dominant. The biochemical properties of these various combinations are not, of course, identical, the polymers in which the natural forms (L) are dominant being more open to enzymatic degradation. It is thus possible to control their degradation by measuring the relative proportions of one form and the other in the copolymer.

The polymer I and copolymer II are insoluble in water and usually soluble in one or more conventional solvents such as acetone, methyl ethyl ketone (MEK). tetrahydrofuran (THF), dioxan, ethyl acetate, monoglyme, diglyme and others, which can be easily transformed into balls, pellets, fibres, filaments, micro capsules. films, etc. Depending on their structure polymers I and II may be insoluble or soluble in chlorinated solvants, such as chloroform. In certain cases of insolubility in chloroform, this can be remedied by adding a small amount of acetone to a solvent of this type. This ability to dissolve in a number of solvents which may or may not be mixable with water, makes them compatible without any other with numerous liquid drugs or drugs which are soluble in the same solvants. Thus, for example, in order to encapsulate a water-soluble product in polymer micro-balls, it is possible to use the known, well-established technique of dispersing an aqueous solution of the drug into a polymer solution, the latter comprising a solvent which cannot be mixed with water, then evaporating this solvent so that solid polymer capsules form.

Furhermore, according to its structure, polymer I is often perfectly compatible with polyalkylene glycols (polyethylene glycol and polypropylene glycol), which means that glycol polyethers can be used as polymer I plasticizers and to thus provide a homogeneous mixture with a low fusion point. It is easy to incorporate a whole gram of thermolabile drugs in a mixture of this type (fusion at temperatures of approximately 40° to 60° C.) and to obtain granules or micro capsules therefrom. Furthermore, the presence of very hydrophilic polyalkylene glycols means that it is possible to increase the susceptibility of the polymer and the copolymer to biological aqueous liquids and to facilitate their in situ enzymatic degradation. It should be noted that known synthetic polypeptides do not have these favourable properties of solubility and of compatibility with PEGs. Thus, for example, to form films of polyglutamate acid having an appreciable mechanical resistance and a certain degree of insolubility in water, it is necessary to use solvents which are relatively awkward to handle and which are not well liked in pharmaceutical circles such as dimethyl formamide (DMF) and dichloroacetic and trifluoroacetic acids (DCA and TFA). The films of polyglutamic acid obtained from aqueous solutions (at pH 7.4, i.e. when the acid is at least partially salified) do not have any mechanical resistance and are quickly dissolved in water, which makes the polymer entirely unsuitable as a carrier of delayed release drugs in the sense of the present invention. The same applies to polyglutamic-polyethylene glycol acid mixtures which are immediately soluble in water.

The biodegradation of polymer I can be represented diagramatically as:

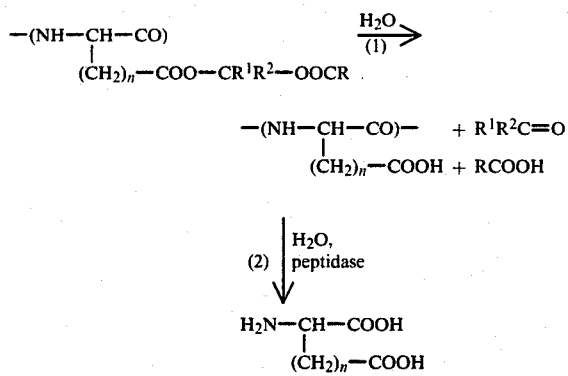

The reaction (2) follows reaction (1) and consequently the rate of polymer biodegradation increases as the rate of the hydrolysis of the lactal or acyloxyalkylic ester increases. The hydrolysis mechanism of esters of this type is known per se and was demonstrated during the study of esters of ampicillin (for example pivampicillin), in this matter see the following references: "Design of biopharmaceutical properties through pro-drugs and Analogs", B. Roche, editor, American Pharmaceutical Association (ISBN 0-917330-16-1). page 212 and 354 (1977). It should be noted that, since $R^2$ is hydrogen and $R^1$ an alkyl (for example methyl), the compound resulting from the reaction (1) is an $R^1$—CHO aldehyde (for example acetaldehyde), these aldehydes being biologically more advantageous than the metaldehyde obtained when $R^1=R^2=H$ for reasons of toxicity. As far as this aspect of the invenrion is concerned, the products resulting from the reaction (1) where R and $R^1$ are interlinked (the ketonic acids or acid aldehydes) are also most advantageous as a result of their negligible toxicity. Thus, if the association R-$R^1$ corresponds to the ethylene or 1,2-phenylene groups, the products of degradation will be respectively, 3-formyl-propionic acid and O-formyl-benzoic acid slowly eliminated by the organism without secondary reactions.

The polymer I can be prepared by direct esterification of a corresponding poly amino acid salt with an acyloxymethyl halide (X—$CR^1R^2$—OCO—R (III)) where X may be chlorine, bromine or iodine. The polyamino acid is preferably a tertiary amino salt (for example of tributylamine or triethylamine). This type of method is known per se by W. V. DACHNE; J. Med chem. 13, 607-12, 1971). Furthermore, the synlhesls of the compounds III (X =Cl) is known (see Z. H. ULICH, J.A.C.S. 43, 662 (1921)) and consists in reacting the acid chloride RCOCl with formaldehyde in the presence of a catalytic quantity of anhydrous $ZnCl_2$.

The polyamino acid or co-polyamino acid of which the esterification products the polymer I or the copolymer II is easily obtained by conventional means consisting of the esterification by a lower alcohol of the lateral carboxyl of an acid having the formula:

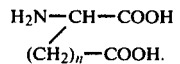

the transfromation of the ester into the corresponding N-carboxyanhydride (NCA) by phosgene in a medium of dioxan or THF, the polymerisation of NCA into esterifed polyamino acid and the hydrolysis of the protector ester group in an alkaline medium or by trifluoroacetic acid. These methods are known per se (see for example Encyclopedia of polymer Science and Technology; N-carboxyanhydrides, vol II, page 837). If it desired to obtain a copolymer where R' designates a partially esterified lateral carboxyl (R'=—$(CH_2)_n$—COOH and R"=—$(CH_2)_n$—COOAlk) care is taken to ensure that the hydrolysis of the protector ester group is only partial. Thus for example the starting product to be esterified with the compound $XCR^1R^2$—OCOR will be a copolymer of acid $H_2N$—CH[$(CH_2)_n$—COOH]—COOH and of ester $NH_2$—CH[$(CH_2)_n$—COO Alk]—COOH.

The polymer I and the copolymer II can be used to store drugs in various ways. Thus for example, the present polymers I and copolymers II can be used to produce microcapsules containing a drug. Microcapsules of this type comprise a polymeric membrane and contain an aqueous or oily solution in which the drug is in suspension or in solution. It is also possible to manufacture microspheres, i.e. solid particles or balls containing the drug in a dispersed state or in the form of solid solution in the polymer matrix. It is also possible to produce microporous products called microsponges. In general, it is possible using the present polymers to apply all the methods of manfacturing delayed release drugs, i.e. drugs having the property of releasing (salting out) the drug in a prolonged manner as the carrier degrades. A description of these methods can be found in the following works: "Biodegradables and Delivery Systems for Contraception", Mafez E. S. E., MTP Press Limited (1980); "Controlled Release Technologies=-Methods, Theory and Applications" Vol. I and II, A. F. Kydonieus, CRC Press (1980) and "Microencapsulation - New Techniques and Applications" by Tamotsu KONDO, Techno Inc. (1979) Japan. The solubility of the present polymers in numerous solvents, which may or may not be mixable with water, is an advantage for their application according to the methods described in these references. It is also possible to prepare threads comprising these polymers by extruding a solution of the latter in a spinneret and by precipitating the thread either by evaporation or by a bath of non-solvent according to conventional methods of extrusion. Threads prepared in this manner may be knitted, knotted or woven to form stitching, ligatures or tubular structures which can act as artificial arteries, veins, ducts or internal organs for temporary operation. The polymers of the invention can also be used either directly or mixed with a plasticizer in the manufacture of films or surgical prostheses for example for mending fractured bones, such as clips, needles, screws, reinforcement plates, wads etc., these materials can be made by solution casting or moulding, thermoforming or by machining solid polymer blocks. since protheses of this type can be reabsorbed, they are gradually eliminated in the organism and it is therefore not necessary to carry out a new operation, as is currently the case, to remove the reinforcement or consolidation material.

Of course, the exact composition of the polymer or copolymer used is to be regulated, as a function of the rates of degradation and the absorbtion characteristics in vivo, according to the type of prosthesis envisaged.

The following examples illustrate the invention.

EXAMPLE 1

Copolymer of benzoyloxymethylene polyglutamate, glutamic acid and methyl glutamate.

Partially methylated polyglutamic acid was prepared from methyl γ-glutamate N-carboxyanhydride dissolved in methylene chloride; triethylamine is used as a polymerisation catalyst (A/l=100). The polymer was then precipitated by adding methanol, then vacuum-dried. The solid was redissolved in trifluoroacetic acid (TFA) so as to produce a solution of 5% by weight and a volume of distilled water was added drop by drop whilst stirring vigorously so that the final solution contained equal volumes of water and TFA. This was then agitated for a further 12-15 hrs. at room temperature (viscous solution), after which the entire contents were poured into a large amount of distilled water, which led to the precipitation of a methyl glutamate and polyglutamic acid copolymer, the hydrolysis of the methyl ester having reached approximately 60-70%. This copolymer Was filtered and dried. The relative proportions of the free and esterified COOH groups of the copolymer obtained by NMR analysis in TFA (integration of the methyl ester band —O—CH$_3$ at 3.95 ppm) were regulated. An analysis of the molecular weight was carried out by GPC (gel permeation chromatography) in DMF on a bimodal DUPONT ZORBAX PSM column (polystyrene calibration); a number average molecular weight Mn of 226.000; and a dispersion (Mw/Mn) of 1.75 were measured.

1.22 g of the copolymer was dissolved in 45 ml of DMF and 3.5 g of tributylamine added. 3.25 g of chloromethyl benzoate prepared according to ULICH, J.A.C.S. 43, 662 (1921) was then added drop by drop and stirring is maintained for 48 hours at room temperature. 50 ml of water was then added, which caused the precipitation of a colourless solid which was filtered, dried and purified by successively dissolving in acetone and precipitating with ether, then dissolving in acetone and precipitation with water. By NMR analysis of the product in TFA, the following resonances were observed: δ=7.8 ppm (4H, aromatic); 8.4 ppm (1H, amido); 6.5 ppm (2H; O—CH$_2$—O); 2-3 ppm (complex, 4H, β—CH$_2$); γ—CH$_2$) 5 ppm (1H, α—CH); 3.95 ppm (CH$_3$ ester). The integration of the spectrum showed that the esterification of the free acid functions by chloromethylbenzoate was approximately 60% and that in the formula of the copolymer as shown below:

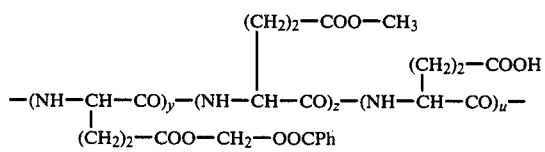

the indices have the following values: y=0.6; z=0.33 and u=0.07.

This polymer is insoluble in water, CH$_2$Cl$_2$, CHCl$_3$ and ether; It expands without dissolving in methanol and ethanol; it dissolves easily in the following solvents: acetone, methylethyl ketone; THF, AcOEt DMF, TFA, dichloracetic acid (DCA). Thin films of the polymer can be prepared by spreading layers of these solution on substrates and allowing them to evaporate.

EXAMPLE 2

Copolymer of partially methylated glutamic acid and of pivaloyloxyethyl glutamate.

Following the process described in the preceding example, a copolymer of glutamic acid and of methyl glutamate was prepared by the gradual hydrolysis of methyl polyglutamate in an aqueous solution of TFA. The copolymer obtained had the formula:

Glu (OME)$_{0.25}$—Glu(OH)$_{0.75}$ 2 g of this copolymer was dissolved in 50 ml of dry DMF and 5.74 g (0.031 mole) of tributylamine and 5.09 g (0.031 mole) of α-chloroethyl pivalate (prepared according to the reference cited in the above example, by the action of pivaloyl chloride on paraldehyde) was added drop by drop. After 4 days of agitation at normal temperatures, this was diluted by a large amount of water, which precipitated the polymer in the form of a colourless powder which was redissolved, after drying, in acetone and reprecipitated with petroleum ether. Two more stages of purification were then carried out by dissolving in acetone and reprecipitating in petroleum ether, which finally produced 1.8 g of the product. By means of NMR analysis it was established that the copolymer had the following formula:

Glu(OMe)$_{0.25}$—Glu(OH)$_{0.6}$—Glu(O—CH(CH$_3$)—OOCt.Bu)$_{0.15}$

The results of the analysis were as follows:
δ=1.35 ppm (s,ter-butyl);=1.7-1.8 ppm (d, —CH(CH$_3$)—); δ=6.8 ppm (—CH(CH$_3$)—)

This polymer is soluble in the solvents mentioned in the preceding example with the exception of chloroform.

EXAMPLE 3

The operations described in the preceeding example were repeated. this time using a copolymer with the formula Glu(OMe)$_{0.5}$—Glu (OH)$_{0.5}$ obtained as described above by the gradual hydrolysis of poly(methyl glutamate), the time of the latter being limited to 6 hrs. It was found that the copolymer corresponded closely to the above-mentioned formula by comparing the integration values of the protons in NMR, the signal at 3.95 ppm (O—CH$_3$) and that at 5 ppm (α—CH).

1 g of this polymer was reacted with 2 equivalents of α—chloroethyl pivalate for three days, and is then precipitated from solution in DMF with water. After purification as described in the preceding example, it was determined by NMR analysis as described above that the formula of the copolymer was as follows:

Glu(OMe)$_{0.5}$—Glu(OH)$_{0.33}$—Glu(OCH(CH$_3$)—OCO—t.Bu)$_{0.17}$

This copolymer is soluble in the above-mentioned solvents and also in CHCl$_3$. It is insoluble in polyethyleneglycol 400.

EXAMPLE 4

3-bromophthalide with the formula

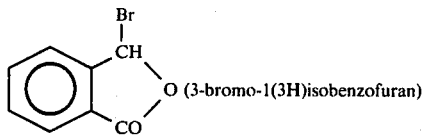

by bromination of phthalide was prepared according to document GB-A-1 364 672, p.5.

2 g of polyglutamic acid and 5.74 g (2 equiv.) of tributylamine were dissolved in 35 ml of dry DMF and 16.7 g of the above bromophtalide was added to this mixture. After a few minutes, there was a considerable thickening of the solution (gel) which was redissolved by adding 5 ml of water. After 6 days of agitation at room temperature, 500 ml of ethanol was added, which caused the precipitation of a colourless powdery product, which was filtered, drained rinsed and dried. The product was redissolved in 40 ml of CHCl$_3$ and purified by precipitating it with ether. Yield 2.77 g (68%). By means of NMR analysis, the following results were obtained:

$\delta = 8$ ppm (4H, Bz+1H, peptid.); $\delta = 7.7$ ppm (CH lactonic); $\alpha = 5$ ppm ($\alpha$—CH); $\delta = 2-3$ ppm (m, —CH$_2$—CH$_2$—).

By comparing after integration the ratio between the 5 proton ($\alpha$—CH) and the aromatic protons it was found that the esterification was 90%. The formula of the product obtained in this manner is:

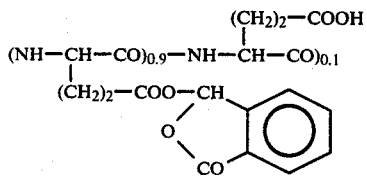

This product, which is highly soluble in CHCl$_3$, is insoluble in water, alcohol, glycol polyethylene and pure acetone. It is soluble in a mixture of acetone —CHCl$_3$.

A dry film of several um* of this polymer was prepared by spreading a chloroform solution on a glass plate and evaporating it. This film was placed in a receptacle oontaining a 0.1N solution buffered at pH 9.5 and there was a slow degradation of the polymer which was observed day by day by the increase in the UV absorbtion of the solution (280 mm) owing to the presence of phthalide which gradually formed in the buffer solution.

EXAMPLE 5

10 g of a 1/1 copolymer of poly($\gamma$-methyl-L-glutamate) and of poly(pivaloyloxymethyl-L-glutamate) prepared according to example 2 was dissolved in 75 ml of chloroform and 5 g of indomethacin (Sigma) was added. A viscous yellow solution was thereby obtained, which was poured drop by drop whilst agitating vigorously into 1 liter of distilled water containing 0.1% of sodium dodecylsulphate (SDS). This solution was agitated at 40° C. until the chloroform is completely evaporated, which led to a dispersion of microspheres. The latter were filtered and separated into batches of different sizes using calibrated sieves. These microspheres dissolve in an isotonic medium (pH 7.5) and, over a long period of time, release the drug which they contain, the rate of release varying according to their average size. When a suspension of this type is injected into a tissue having an inflammatory infection, the action of the drug is much longer than that of a conventional drug with an indomethacin based drug.

EXAMPLE 6

Poly (pivaloyloxymethy glutamate)

Polyglutamic acid was prepared from methyl $\gamma$-qlutamate N-carboxyanhydride dissolved in methylene chloride; triethylamine was used as a polymerisation catalyst (A/T=100). The polymer was then precipitated by adding methanol, then vacuum dried. The solid was redissolved in trifluoracetic acid (TFA) so as to produce a solution of 5% by weight and a measure of distilled water was added drop by drop whilst stiring vigorously, the measure being sufficient so that the final solution contained equal volumes of water and TFA. Agitation was maintained for a further 24 hrs. at room temperature (viscous solution). after which the entire contents were poured onto a large amount of distilled water, which led to the precipitation of the polyglutamic acid. This acid was filtered and dried. The purity of the acid thus obtained was checked by NMR analysis in TFA (absence of the methyl ester band —O—CH$_3$ at 4.5 ppm). an analysis of the molecular weight was carried out by GPC (gel permeation chromatography) in DMF on bimodal DUPONT ZORBAX PSM column (polystyrene calibration) and the following values were measured: $M_n = 226.000$; $M_w = 397.000$; $M_z = 723.000$; dispersivity=1.75.

The polyacid was dissolved in DMF at a level of 5% by weight and at 50 ml of this solution, 4 ml of water and 4.04 (0.04 mol) of triethylamine was added. Firstly there was a precipitation of triethylamine polyglutamate, the salt then dissolving again by agitation when water was added. When everything was dissolved 6.02 g of chloromethyl pivalate (Fluka Ag) was added drop by drop and agitation was continued for 48 hours at room temperature. 50 ml of water was then added, which caused the precipitation of a colourless solid which was filtered, dried and purified successively by dissolution in acetone and precipitation with water. By means of NMR analysis of the product in TFA, the presence of a tertbutyl peak at 1.35 ppm was observed. Integration of the spectrum revealed that the esterification of the polyglutamic acid was total. The molecular weight was determined as above and provided the following results: $M_n = 30.480$: $M_w = 708.000$; $M_z = 297.000$; dispersivity=3.54 (relative viscosity $\eta = 1.57$ C=0.2 g/dl in DMF). Final yield 51%.

This polymer is insoluble in water, CH$_2$, CHCl$_3$ and ether; it expands without dissolving in methanol and ethanol; it dissolves easily in the following solvents: acetone. methylethyl ketone; THF, AcOEt/DMF, TFA dichloracetic acid (DCA). Thin films of polymer can be prepared by spreading layers of these solutions on substrates and allowing them to evaporate. The IR spectrum also confirms the proposed structure (wide band at 1740 cm$^{-1}$).

EXAMPLE 7

A thin film of polymer obtained according to example 6 was prepared by spreading a layer of 10% solution in acetone and allowing it to dry for several hours at ordinary temperature in air.

Several samples of the film were then immersed in a solution of 1% pancreatine in 0.1 M phosphate buffer (pH 7.5) and the samples were left at room temperature from 1 to 8 days. After 1 day a noticeable loss of mechanical resistance (approx. 50%) was observed and after 2 days, almost total disappearance of this resistance (the sample broke into pieces). After 8 days, the sample had completely decomposed and was no longer visible. Similar results were observed using esterase or leucinaminopeptidase.

EXAMPLE 8 prearation of a copolymer ester of pivaloyloxymethyl glutamic and leucine

The procedure was as in example 6, but starting with an 85/15 copolymer of polyglutamic acid and leucine and an 85/15 copolymer of pivaloyloxymethyl glutamate/leucine was obtained. The NMR spectrum of the polymer in solution in TFA shows that 100% of the lateral carboxylic groups of polyglutamic acid are esterified by chloromethylpivalate. The polymer is also soluble in acetone, MEK, DMF, THF. It expands in alcohol without dissolving. NMR spectrum: $\delta = 1.35$ ppm, 9 tert-butyle protons; $\delta = 1, 0, 6$-isobutyle protons. Integration: ratio of groups 85:15.

EXAMPLE 9 preparation of isobutyloxylmethyl glutamate ester polymer

Synthesis was carried out starting with polyglutamic acid prepared as described in example 6; this polymer was dissolved in DMF previously dried on molecular sieve so as to obtain a 3.2% solution. To 20g of this solution, 1.83g of tributylamine (2 equivalents) was added. In contrast to what was observed with triethylamine, it is not necessary to add water for dissolution. 1.36g of the chloromethyl ester of isobutyric acid (prepared in accordance with ULICH, J.A.C.S. 43, 662, (1921) (b.p. 65° C./48 Torr) is then added drop by drop to the solution of tributylamine polyglutamate and is left for 3 days, subject to shaking, at room temperature. The reaction mixture is then precipitated by water, dissolved again in acetone. precipitated aqain with hexane, dissolved again in acetone and precipitated again with water. The RMR analysis of the dried polymer reveals the presence of isobutyl peaks ($\delta = 1.15$ ppm, doublet) characteristic of the product researched and, by integration 90% substitution (obtained 1.03 g, 90%). The polymer is also soluble in acetone, MEK, THF, DMF. Both the infrared spectrum of a film cast from a solution of TFA, and the elementary analysis correspond to the proposed structure.

EXAMPLE 10

Pharmaceutical preparation based on poly(pivaloyloxymethyl glutamate) plasticised PEG 5g of poly(pivaloyloxymethyl glutamate) and 5g of polyethyleneglycol 600 (Fluka, AG) and 2 g of indomethacin (Sigma) are dissolved in 100 ml of acetone. A film is cast from this solution onto a glass plate and the solvent is left to evaporate. The film obtained, heated to 50° C., melts and can be moulded in to the form of capsules which, once cooled and immersed in an isotonic aqueous solution, allows indomethacin to diffuse into the medium.

EXAMPLE 11

Synthesis of poly(acetoxymethyl glutamate)

The synthesis was carried out as in example 9, but starting with chloromethyl acetate.

The polymer obtained is also soluble in acetone. Its NMR spectrum shows the presence of a peak at 3.2 ppm, which is characteristic of the acetyl group (3 protons). The polymer dissolves in aqueous caustic soda N/100, being hydrolysed in a few minutes.

EXAMPLE 12

In vitro biodegradation of poly(pivaloyloxymethyl glutamate)

Poly(pivaloyloxylmethyl glutamate). the methyl group of which is labelled at $^{14}C$, was prepared in accordance with example 6. For this purpose chloromethylpivalate was synthesised by causing pivaloyl chloride to react on paraformaldehyde labelled with $^{14}C$, according to the technique described in J.A.C.S., 89 (21), 5442, (1967).

The specific activity of the polymer, measured by combustion, is 3 uCie/g. $3 \times 3$ cm films were prepared from this polymer from solutions in acetone or in TFA. The films obtained are soaked either in enzymatic solutions of Leucineaminopeptidase from pig kidney (Sigma, 3.7 Units/ml, 0.1 buffer grades, 5 mM MgCl$_2$, pH 8.4), or esterase from pig liver, (Sigma, 11.6 Units/ml, 0.1M buffer Grades. pH 7.5). The speed of degradation is measured by observing on the one hand the appearance of the polymer, and on the other hand, by counting the degree of radioactivity acquired by the solution. The enzymatic solutions were renewed each day. The following results were obtained.

| Incubation time film drained from a solution of: | Esterase (pH 7,5) Acetone | (pH 8,4) Leucine Aminopeptidase | |
|---|---|---|---|
| | | Acetone | TFA |
| 1 day | opaque film, 3.5% hydrolysis | opaque film, 13.6% hydrolysis | opaque film, 12.6% hydrolysis |
| 2 days | whitish, blown film, 9% hydrolysis | opaque film 29% hydrolysis | film very deformed 46.8% hydrolysis |
| 4 days | whitish, blown, film, 17% hydrolysis | opaque, blown, film, 52% hydrolysis | film disintegrated, dissolved, some solid debris 85% hydrolysis |
| 5 days | expanded film, 24% hydrolysis | film begins to to break down, 71% hydrolysis | |
| 7 days | gelatinous film 37% hydrolysis | film completely disintegrated 85% hydrolysis | |

EXAMPLE 13

Poly(pivaloyloxymethyl glutamate) is dissolved in acetone and 10% by weight of polyethyleneglycol polymer 600 is added. The solution is flowed onto a Teflon plate and a the solvent is left to evaporate. The film obtained is translucent and can be welded thermally at approximately 120° C.

Example 14

A polymer of aspartic acid and leucine (see Polymer 16, 735 (1975)) was prepared by copolymerising β-benzylaspartate NCA and leucine NCA (N-carboxyanhydrides) in equimolecular proportions. Benzyl ester groups are are transesterified by methanol in order to obtain the copolymer poly-(β-methylaspartate/leucine). The methyl ester groups are then saponified by N/10 soda in methanol to obtain the acid poly-(ASP-(OH)/leu). Analysis of the amino acids shows that there is a leucine proportion of 56% and 44% for aspartic acid. The molecular weight $M_n$ is 35,000 (measured by GFC).

1 g of poly-(Asp(OH)/leu) is dissolved in 20 g of dry DMF. 3.25 g of tributylamine (4 equivalents relative to the Asp (OH) groups) and 2.64 g of chloromethylpivalate (4 equivalents). This is left for 3 days, being agitated at room temperature. The polymer is precipitated in distilled H2O, is dissolved again in acetone, precipitated in petroleum ether, dissolved again in acetone and preciptated again with H2O. It is then dried. NMR analysis shows that poly-(pivaloxymethylaspartate/leucine has indeed been obtained, the esterification rate being approximately 20% (δ=7.5 benzylic protons; δ=8 ppm. NH protons; δ=5.4 and 4.8, alpha-CH protons; δ=3.95, O—CH3 non-saponified protons: δ=3.3 and 2, —CH2— protons, δ=1.35 ppm. t-butyl protons). Despite the relatively low esterifioation rate, the copolymer is soluble in acetone.

EXAMPLE 15

For purposes of comparison, there were studied the hydrolysis speeds in an alkaline medium of a copolymer according to the invention, labelled as described in example 7, (pivaloyloxymethyl-leucine glutamate copolymer 85-15 according to example 8) and a methyl leucine glutamate polymer 85-15 of the prior art prepared using the usual known techniques by means of methanol labelled with 14C The polymer according to the invention (A) was converted into a film of approximately 0.25 mm by placing a layer of acetone solution on a glass plate, which was then subjected to evaporation in air. The same procedure was followed for the control film (B) starting with a solution in TFA acid. This film was washed carefully in water in order to eliminate any traces of TFA.

The films (A) and (B) were immersed in pH 9.5 aqueous solutions (phosphate buffer), being slowly agitated, and the radioactivity of the products dissolved in the solutions was measured at intervals, on which basis the hydrolysis rate of the polymers subjected to the test was calculated.

The following results were obtained, expressed as a % per weight hydrolysed substance after a given time (hours).

| Sample (A) | | Sample (B) | |
| --- | --- | --- | --- |
| time (hrs.) | % per weight | time (hrs.) | % per wt. |
| 1.5 | 2.8 | 18 | 1.8 |
| 2.5 | 5.0 | 42 | 4.2 |
| 4.5 | 13.2 | 64 | 5 |
| 8 | 37.25 | 88 | 5.9 |
| 8 | dissolution | 112 | 6.8 |

It can be seen from the above results that the copolymer (A) decomposes to such an extent in 8-10 hours that the drug which it might have contained would have dissolved completely in such conditions, whereas the prior art copolymer is only slightly decomposed after 112 hours in the same conditions.

By varying the leucine rate of the copolymer (A), the hydrolysis time can be varied, for an increase by increasing the said rate and for a decrease by reducing the said rate.

I claim:

1. A poilypeptide selected from the group consisting of (a) biodegradable polymers with the formula

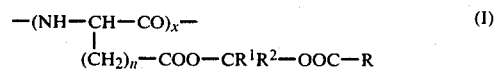

in which $R^1$ and $R^2$ are selected from the group consisting of lower alkyl and hydrogen; and R is lower alkyl or an aromatic radical; or $R^2$ is lower alkyl or hydrogen and R and $R^1$ are interlinked in the form of a substituted or non-substituted ethylene or vinylene bridge; and (b) polymers with the formula

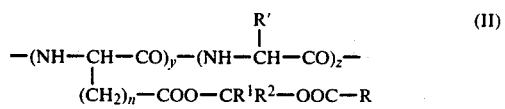

in which groups R, $R^1$ and $R^2$ have the values given above and where R' is a free or partially or completely esterified amino-acid radical; y and z are integers, n is 1 or 2; and x is equal to y+z and is selected so that the molecular mass of the polypeptide is not lower than 5000D.

2. Polypeptide according to claim 1 wherein R is selected from the group consisting of methyl, ethyl, isopropyl, isobutyl, tert-butyl, phenyl and benzyl radicals.

3. Polypeptide according to claim 1 wherein R and $R^1$ are interconnected to form a link selected from the following formulae: —CH2—; —C=CH—; —CH(CH3)—CH(CH3); —C(CH3)=C(CH3)—; 1.2-phenylene; cyclohexenylene; cyclopentenylene, cyclopentadienylene.

4. Polypeptide according to claim 1 wherein polymer (I) is selected from acyl- and aryloxymethyl glutamates and aspartates and polymers (II) is selected from acyl- and aryloxymethyl glutamate or aspartate copolymers with one or more other amino-acids selected from alanine, leucine, valine and phenylalaline.

5. Polypeptide according to claim 1 wherein polymers (II) is a glutamate or aspartate copolymer with at least one member of the group consisting of glutamic acid, lower alkyl glutamates, aspartic acid and lower alkyl aspartates.

6. Polypeptide according to claim 4 wherein the acyl groups are selected from acetyl, propionyl, butyryl, isobutyryl, pivaloyl, benzoyl, and phenylacetyl groups.

7. A drug composition comprising a polypeptide selected from the group consisting of (a) biodegradable polymers with the formula

in which $R^1$ and $R^2$ are selected from the group consisting of lower alkyl and hydrogen; and R is lower alkyl or an aromatic radical; or $R^2$ is lower alkyl or hydrogen and R and $R^1$ are interlinked in the form of a substituted or non-substituted ethylene or vinylene bridge; and (b) polymers with the formula $$-(NH-\underset{(CH_2)_n-COO-CR^1R^2-OOC-R}{\underset{|}{CH}}-CO)_y-(NH-\underset{|}{\overset{R'}{CH}}-CO)_z- \quad (II)$$

in which groups R, $R^1$ and $R^2$ have the values given above and where $R^1$ is a free or partially or completely esterified amino-acid radical; y and z are integers, n is 1 or 2, and x is equal to y+z and is selected so that the molecular mass of the polypeptide is not lower than 5000D, and a drug, the polypeptide serving as a drug reservoir with a delay effect, the drug being released progressively to its destination consequent upon the biodegradation of the polypeptide.

8. A composition according to claim 7 wherein the drug and the said polypeptide are mixed homogeneously and shaped in a pharmaceutically acceptable form.

9. A composition according to claim 8 which includes polyalkylene glycol to plasticise the polypeptide.

10. A biodegradable implant or prosthetic comprising the composition of claim 7.

11. In a method of administering a drug by release from a biodegradable polymer carrying the drug, the improvement which comprises using a polypeptide selected from the group consisting of (a) biodegradable polymers with the formula $$-(NH-\underset{(CH_2)_n-COO-CR^1R^2-OOC-R}{\underset{|}{CH}}-CO)_x- \quad (I)$$

in which $R^1$ and $R^2$ are selected from the group consisting of lower alkyl and hydrogen; and R is lower alkyl or an aromatic radical; or $R^2$ is lower alkyl or hydrogen and R and $R^1$ are interlinked in the form of a substituted or non-substituted ethylene or vinylene bridge; and (b) polymers with the formula $$-(NH-\underset{(CH_2)_n-COO-CR^1R^2-OOC-R}{\underset{|}{CH}}-CO)_y-(NH-\underset{|}{\overset{R'}{CH}}-CO)_z- \quad (II)$$

in which groups R, $R^1$ and $R^2$ have the values given above and where $R^1$ is a free or partially or completely esterified amino-acid radical; y and z are integers, n is 1 or 2, and x is equal to y+z and is selected so that the molecular mass of the polypeptide is not lower than 500D, as the carrier for the drug.

* * * * *